(12) United States Patent
Merfeld et al.

(10) Patent No.: US 8,430,823 B2
(45) Date of Patent: Apr. 30, 2013

(54) VESTIBULAR CANAL PLUG

(75) Inventors: Daniel Michael Merfeld, Lincoln, MA (US); Wangsong Gong, Revere, MA (US); Steven D. Rauch, Watertown, MA (US); Richard Terry, Arlington, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 0 days.

(21) Appl. No.: 13/233,111

(22) Filed: Sep. 15, 2011

(65) Prior Publication Data

US 2012/0000474 A1   Jan. 5, 2012

Related U.S. Application Data

(63) Continuation of application No. 11/195,568, filed on Aug. 1, 2005, now abandoned.

(51) Int. Cl.
*A61B 5/00* (2006.01)
*A61B 19/00* (2006.01)
*A61M 29/00* (2006.01)

(52) U.S. Cl.
USPC ........... 600/559; 128/898; 606/191; 606/192; 600/37

(58) Field of Classification Search ................. 128/897, 128/898; 600/37, 25, 553, 559; 601/191, 601/192
See application file for complete search history.

(56) References Cited

U.S. PATENT DOCUMENTS

| | | | |
|---|---|---|---|
| 4,558,703 A | 12/1985 | Mark |
| 4,592,359 A | 6/1986 | Galbraith |
| 4,754,748 A | 7/1988 | Antowski |
| 5,658,322 A | 8/1997 | Fleming |
| 5,919,149 A | 7/1999 | Allum |
| 5,922,016 A | 7/1999 | Wagner |
| 5,951,596 A | 9/1999 | Bellinger |
| 5,984,859 A | 11/1999 | Lesinski |
| 6,063,046 A | 5/2000 | Allum |
| 6,078,838 A | 6/2000 | Rubinstein |
| 6,219,578 B1 | 4/2001 | Collins et al. |
| 6,219,580 B1 | 4/2001 | Faltys et al. |
| 6,295,472 B1 | 9/2001 | Rubinstein et al. |
| 6,314,324 B1 | 11/2001 | Lattner et al. |
| 6,358,272 B1 | 3/2002 | Wilden |
| 6,430,443 B1 | 8/2002 | Karell |
| 6,546,291 B2 | 4/2003 | Merfeld et al. |
| 6,735,475 B1 | 5/2004 | Whitehurst et al. |

(Continued)

FOREIGN PATENT DOCUMENTS

WO   2004/045242   5/2004
WO   2004/060015   7/2004

OTHER PUBLICATIONS

Merriam-Webster's Collegiate Dictionary, 10th ed. 2001, Merriam-Webster, Incorporated. p. 370.

(Continued)

*Primary Examiner* — Max Hindenburg
*Assistant Examiner* — Jonathan M Foreman
(74) *Attorney, Agent, or Firm* — Fish & Richardson P.C.

(57) ABSTRACT

An apparatus to reduce the sensitivity of the vestibular system to stimulation. The apparatus comprises a plugging device configured to constrain the movement of endolymph fluid within a semicircular canal, and a control module coupled to the plugging device that causes the plugging device to maintain a set actuated position.

6 Claims, 3 Drawing Sheets

U.S. PATENT DOCUMENTS

| | | |
|---|---|---|
| 6,748,275 B2 | 6/2004 | Lattner et al. |
| 6,830,580 B2 | 12/2004 | Neuberger |
| 6,921,413 B2 | 7/2005 | Mahadevan-Jansen et al. |
| 7,225,028 B2 | 5/2007 | Della Santina et al. |
| 7,488,341 B2 | 2/2009 | Merfeld |
| 7,730,892 B2 | 6/2010 | Merfeld et al. |
| 2002/0072781 A1 | 6/2002 | Lattner et al. |
| 2003/0171787 A1 | 9/2003 | Money et al. |
| 2003/0195588 A1 | 10/2003 | Fischell et al. |
| 2004/0006287 A1 | 1/2004 | Epley |
| 2004/0167415 A1 | 8/2004 | Gelfand et al. |
| 2004/0199223 A1 | 10/2004 | Andersen et al. |
| 2004/0215236 A1 | 10/2004 | Lattner et al. |
| 2005/0201574 A1 | 9/2005 | Lenhardt |
| 2005/0216072 A1 | 9/2005 | Mahadevan-Jansen et al. |
| 2005/0222644 A1 | 10/2005 | Killian et al. |
| 2005/0267549 A1 | 12/2005 | Della Santina et al. |
| 2006/0004422 A1 | 1/2006 | De Ridder |
| 2006/0079950 A1 | 4/2006 | Lehnhardt et al. |
| 2006/0161227 A1 | 7/2006 | Walsh et al. |
| 2006/0161255 A1 | 7/2006 | Zarowski et al. |
| 2007/0012321 A1 | 1/2007 | Zelinsky |
| 2007/0100263 A1 | 5/2007 | Merfeld |
| 2007/0167985 A1 | 7/2007 | Kirby |
| 2008/0172102 A1 | 7/2008 | Shalev |

OTHER PUBLICATIONS

Rabbitt RD, Boyle R, Highstein SM, The influence of surgical plugging on horizontal semicircular canal mechanics and afferent response dynamics. J Neurophysiology, 82:1033-1052, 1999.

Notification Concerning Transmittal of the International Preliminary Report on Patentability for International Application No. PCT/US2006/028756 dated Mar. 19, 2009.

International Search Report for International Application No. PCT/US2006/35759 dated Jul. 27, 2007.

Notification Concerning Transmittal of International Preliminary Report on Patentability for International Application No. PCT/US2006/35759 dated Mar. 27, 2008.

Notification Concerning Transmittal of International Preliminary Report on Patentability for International Application No. PCT/US2006/027535 dated Feb. 7, 2008.

International Search Report for International Application No. PCT/US2006/028756 dated Jun. 30, 2008.

Written Opinion of the International Searching Authority for International Application No. PCT/US2006/027535, dated Jul. 25, 2007.

Notification Concerning Transmittal of International Preliminary Report on Patentability for International Application No. PCT/US2006/35759 dated Jul. 26, 2008.

Wells, et al. "Optical stimulation of neural tissue in vivo." Optics Letters 30(5):504-506, Mar. 1, 2005.

Gong, et al. "Prototype Neural Semicircular Canal Prosthesis Using Patterned Electrical Stimulation". Annals of Biomedical Engineering, vol. 28, pp. 572-581, 2000.

"System Design and Performance of a Unilateral Horizontal Semicircular Canal Prosthesis" by Gong, et al., IEEE Transactions on Biomedical Engineering, vol. 49, No. 2, Feb. 2002, pp. 175-181.

Merfeld, et al. "Ch. 7.7—*Vestibular Prosthetics*". Neuroprosthetics: Theory and Practice, K. Horch and G.Dhillon, Editors. 2002.

Wall, et al. "Vestibular Prostheses: the Engineering & Biomedical Issues". Journal of Vestibular Research 11:1-19, 2002.

VESTIBULAR CANAL PLUG

CROSS-REFERENCE TO RELATED APPLICATIONS

This application is a continuation of and claims the priority of U.S. application Ser. No. 11/195,568, filed on Aug. 1, 2005, the contents of which are hereby incorporated by reference.

TECHNICAL FIELD

This invention relates to a medical plugging device, and more particularly to a vestibular canal plug.

BACKGROUND

The ability of human beings to maintain stability and balance is controlled by the vestibular system. This system provides the central nervous system with the information needed to maintain balance and stability.

Figure 1:
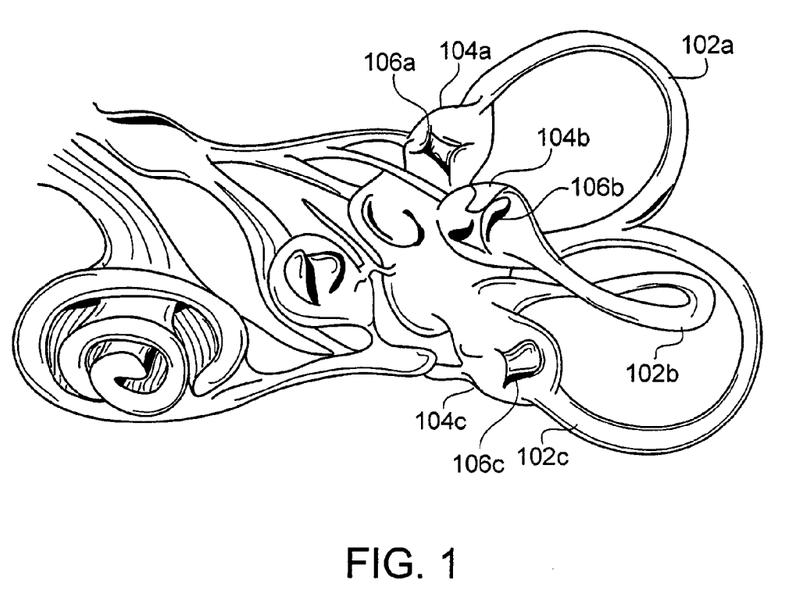
FIG. 1 is a diagram of part of the vestibular system.

In FIG. 1, the vestibular system includes three mutually-orthogonal ring-shaped tubes, referred to as the semicircular canals 102a-c, that are filled with endolymph fluid. The semicircular canals are formed by a membrane called the membranous labyrinth. Each of the semicircular canals 102a-c is disposed inside a hollow bony tube (not shown in the diagram), called the bony labyrinth, that extends along the contours of the semicircular canals. Lining the interior walls of the bony labyrinth is a thin membrane called the endosteum. The bony labyrinth is filled with a fluid called the perilymph.

As further shown in FIG. 1, each semicircular canal 102a-c terminates in an enlarged balloon-shaped section called the ampulla (marked 104a-c in FIG. 1). Inside each ampulla is the cupula 106a-c, on which hair cells are embedded.

Generally, as the semicircular canals 102a-c rotate due to rotational motion of a head, the endolymph fluid inside the canal will lag behind the moving canals, and thus cause the hair cells on the cupula to bend and deform. This deformation stimulates nerves attached to the hair cells, resulting in the generation of nerve signals that are sent to the central nervous system. These signals are decoded to provide the central nervous system with motion information.

The three canals together provide information about rotation in all three spatial dimensions. The other endorgans in the vestibular system are the otolith organs, the utricle and the saccule. These endorgans act as linear accelerometers and respond to both linear motion and gravity.

In response to the vestibular nerve impulses, the central nervous system perceives motion and, in response, controls the movement of various muscles in an effort to maintain balance.

Dehiscence is a medical condition in which the bony labyrinth surrounding one or more of the semicircular canals is so thin that small changes of air pressure in the ear (for example, resulting from sound waves), can cause the actuation of the endosteum that stimulates the vestibular system.

Another condition affecting the vestibular system is intractable benign paroxysmal positional vertigo. In this medical condition, small stones or debris formed in the semicircular canals are randomly displaced inside the endolymph fluid. This disturbs the endolymph fluid, which in turn deflects the hair cells on the cupula. Thus, the patient perceives motion that is inconsistent with his actual motion.

Person suffering from dehiscence, intractable benign paroxysmal positional vertigo, or other conditions resulting in an overly sensitive vestibular system, experience vertiginous symptoms such as dizziness and disorientation.

Occasionally, symptoms associated with dehiscence or intractable benign paroxysmal positional vertigo subside either by themselves, or with the aid of non-invasive treatment (e.g., simple head exercises to remove the debris from the endolymph fluid in situations involving intractable benign paroxysmal positional vertigo). However, in some situations it becomes necessary to perform a surgical procedure called "canal plugging" to alleviate such conditions. The goal of canal plugging is to block most of the canal's function without significantly affecting other semicircular canals or parts of the ear. This procedure, however, poses a small risk to hearing. More troubling, however, is that canal plugging is irreversible. Thus, although canal plugging permanently relieves vertiginous symptoms, it does so at the cost of making it non-feasible for patients to benefit from newly-discovered treatment options.

SUMMARY

The invention is based on the recognition that one can relieve the symptoms of certain vestibular dysfunctions by curtailing flow of endolymph.

In one aspect, the invention includes an apparatus to reduce the sensitivity of the vestibular system to stimulation. The apparatus includes a plugging device configured to constrain the movement of endolymph fluid within a semicircular canal, and a control module coupled to the plugging device that causes the plugging device to maintain a set actuated position.

In some embodiments, the apparatus also includes a sensing system that provides information to the control module indicative of environmental conditions and/or performance of the plugging device.

In other embodiments, the control module is configured to cause the plugging device to maintain the set actuated position by generating a control signal for transmission to the plugging device.

In yet other embodiments, the plugging device includes a balloon attached to a catheter, the balloon having a volume that varies in response to a control signal. In some of these embodiments, the control module is configured to maintain the balloon at the set actuated position by changing the volume of the balloon in response to fluid leakage from the balloon and/or air pressure changes.

Additional embodiments include those in which the plugging device includes a piezoelectric mechanical vibrator configured to be displaced in response to a control signal, a piston, configured to be displaced in response to a control signal, or an elastic membrane, configured to expand in response to a control signal.

In some embodiments, the apparatus also includes a power source electrically coupled to the plugging device to power the plugging device.

In another aspect, the invention includes a method for reducing the sensitivity of the vestibular system to stimulation. The method includes inserting a plugging device in mechanical communication with a semicircular canal of a patient, and maintaining the plugging device at a set actuated position selected to constrain the movement of the endolymph fluid in the semicircular canal.

In another aspect, the invention includes an apparatus for reducing the sensitivity of the vestibular system to stimulation. The apparatus includes one or more plugging devices configured to constrain the movement of endolymph fluid in the corresponding semicircular canals, and a control module coupled to the one or more plugging devices that causes the one or more plugging devices to maintain corresponding set actuated positions.

The details of one or more embodiments of the invention are set forth in the accompanying drawings and the description below. Other features, objects, and advantages of the invention will be apparent from the description and drawings, and from the claims.

DESCRIPTION OF THE DRAWINGS

Like reference symbols in the various drawings indicate like elements.

DETAILED DESCRIPTION

Figure 2:
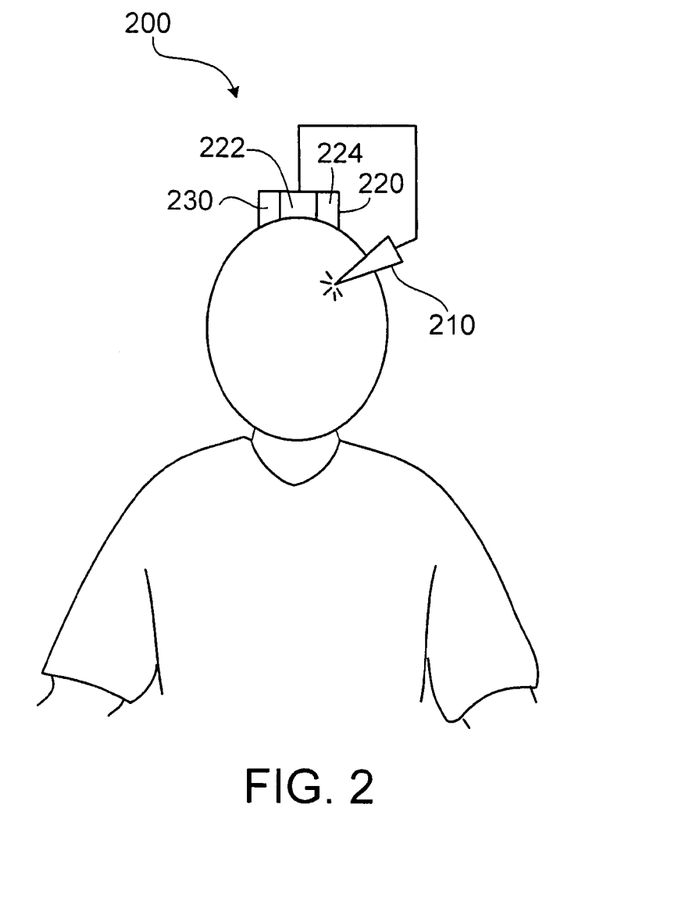
FIG. 2 is a schematic diagram of an exemplary embodiment of a plug apparatus.

FIG. 2 is a schematic diagram of an exemplary embodiment of a vestibular canal plug apparatus 200 to chronically constrain the movement endolymph fluid within the semicircular canal. The plug apparatus 200 includes a plugging device 210 inserted proximate to a semicircular canal with respect to which the flow of the endolymph fluid in that canal is to be constrained.

Figure 3A:
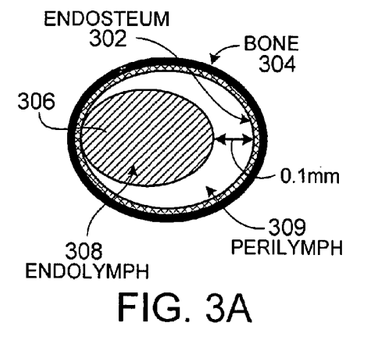
FIG. 3A is a schematic diagram in cross-section of a semicircular canal in the vestibular system.

FIG. 3A is a simplified cross-sectional diagram showing a semicircular canal. As shown, the semicircular canal 306 is formed from the membranous labyrinth.

Endolymph fluid 308 fills the canal 306. A bony labyrinth 304 lined with endosteum 302 defines a volume filled with perilymph fluid 309 that surrounds the canal 306. Actuation of the plugging device 210 to a set position partially or completely pinches the semicircular canal 306 inside the perilymph-filled volume formed by the bony labyrinth. As a result, the diameter of the semicircular canal 306 decreases, and the flow of the endolymph fluid 308 is thus constrained. Consequently, the flow of endolymph fluid in the cupula is also constrained, thereby minimizing the motion of the hairs in the cupula. This in turn reduces stimulation of the central nervous system. When the semicircular canal is completely blocked (i.e., when the semicircular canal is pinched so that at that location the canal's diameter is substantially zero), the endolymph flow in the semicircular canal is effectively inhibited.

The plugging device 210 includes a control mechanism (not shown) that receives control signals transmitted from the control module 220. The control mechanism controls the movement and position of the actuated plugging device, and thereby enables occasional adjustments of the actuated position of the device. Such adjustments may be needed to compensate for disturbances such as fluid leakage, changes in ambient air pressure, and temperature changes. Transmission of control signals from the control module 220 to the plugging device 210 can be done using wireless transmission. Alternatively, the control signals can be sent from an electrical wire connecting the control module 220 to the plugging device 210. The wire is placed such that it runs subcutaneously from the control module 220 to the control mechanism of the plugging device 210.

FIGS. 3B-3E are various embodiments of the plugging device 210. In the embodiment shown in cross-section in FIG. 3B, a plugging device 310 includes a piston 312 that is displaced hydraulically inside a cylinder 316. The dimensions of the mechanical piston depend on the size of the semicircular canal, which in turn depends on the patient's age and gender. A typical piston diameter for an adult male is 0.3-1.0 mm.

Figure 3B:
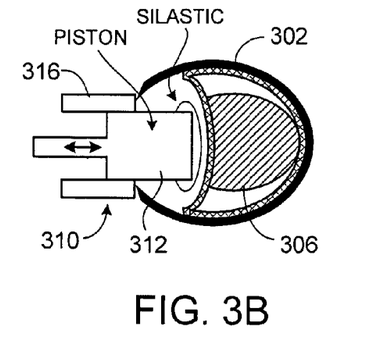
FIG. 3B is a schematic diagram in cross-section of an embodiment of a piston-based plugging device.

Initially, the plugging device 310 receives control signals corresponding to the position to which the piston 312 should be moved to pinch the semicircular canal 306.

As the piston moves to its actuated position, it presses against the endosteum 302. This causes the endosteum 302 to be displaced inwardly. As the endosteum 302 is displaced, it presses against the semicircular canal 306 and pins it against the opposite wall of the endosteum, thereby constraining the canal's motion and altering the dimensions of the semicircular canal 306. The reduced dimensions of the semicircular canal 306 constrain the movement of the endolymph fluid in the semicircular canal 306. As shown in the example of FIG. 3B, the piston 312 is actuated to a position in which the semicircular canal 306 is held in place between the opposing walls of the endosteum 302, but is not entirely pinched. Thus, although the motion of the endolymph fluid in the semicircular canal 306 is constrained, it is not entirely curtailed. In that position, the semicircular canal is only partially blocked. To entirely curtail the flow of the endolymph fluid in the semicircular canal 306, the piston 312 is actuated into a position whereby the piston 312 exerts sufficient pressure on the endosteum 302 to completely pinch the semicircular canal 306, and thus completely block endolymph flow.

The plugging device 310 also includes a control mechanism (not shown) adapted to receive control signals from the control module 220. These control signals cause displacement of the piston 312 in the cylinder 316 to a set actuated position. Thereafter, the position of the piston 312 is maintained, except to adjust for minor positional shift of the piston 312 caused by environmental fluctuations (e.g., fluctuations in temperature or pressure), or by performance degradation of the plugging device 310. The set actuated position of the piston 312 may be occasionally changed in accordance with medical necessities (e.g., to more forcefully pinch the semicircular canal 306).

To minimize damage to the endosteum 302 due to the piston's motion, the piston head is covered with a soft biocompatible material 314. A suitable biocompatible material is Silastic.

Since the plugging device 310 is implanted, it should be constructed using biocompatible materials. Thus, in some embodiments the piston-based plugging device 310 is made of suitable metallic materials such as stainless steel or titanium. Other suitable materials include various types of ceramics that are approved for medical applications.

Figure 3C:
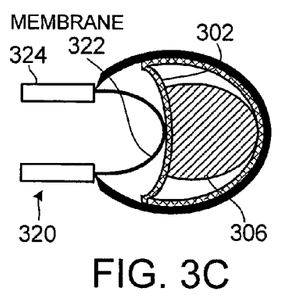
FIG. 3C is a schematic diagram in cross-section of an embodiment of an elastic membrane plugging device.

FIG. 3C shows, in cross-section, a second exemplary embodiment of a plugging device. In the embodiment shown in FIG. 3C, a plugging device 320 includes an elastic membrane 322 placed at the end of a cylinder 324. Pressure provided by a pump mechanism coupled to the plugging device via the cylinder 324 causes the membrane 322 to expand outwardly towards the endosteum 302, thereby deflecting the endosteum 302. As with the piston-based plugging device shown in FIG. 3B, the deflected endosteum 302 presses against the semicircular canal 306 and pins it to the opposite wall of the endosteum 302. The pressure from the actuated membrane 322 deforms the dimensions of the semicircular canal, thereby reducing the space in which the endolymph fluid 308 can flow. The altered dimensions of the semicircular canal constrain, or all together preclude, movement of the endolymph fluid. This reduces the stimulation that can be delivered to the hair cells on the cupula of the semicircular canal 306, thereby reducing the sensitivity of the vestibular system to stimulation. In FIG. 3C, the membrane 322 is shown to have been expanded enough to partially pinch the semicircular canal 306. As noted, however, it is often necessary to completely curtail the flow of endolymph fluid in the semicircular canal 306. Under those circumstances, the membrane 322 is actuated to a position in which it completely pinches the semicircular canal 302, and thus completely blocks the flow of the endolymph fluid in the semicircular canal 306.

The plugging device 320 also includes a control mechanism (not shown) adapted to receive control signals from the control module 220. These control signals cause the plugging device's pump to pump fluid (gas and/or liquid) to expand the elastic membrane 322 to a set actuated position. Thereafter, the position of the elastic membrane 322 is maintained, except to adjust for minor changes to the position of the membrane 322 to compensate for such factors as leakage, or changes in air pressure or temperature, or to adjust the position of the membrane 322 in accordance with medical necessities.

Figure 3D:
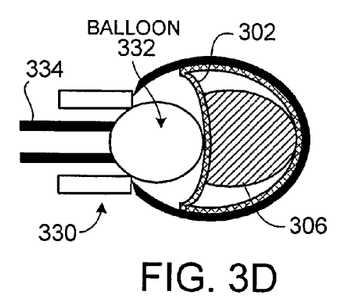
FIG. 3D is a schematic diagram in cross-section of an embodiment of a balloon plugging device implanted at the exterior of the bony labyrinth.

FIG. 3D shows, in cross-section, a third embodiment of a plugging device that includes a balloon 332 in fluid communication with a balloon catheter 334. Pressure provided by a pump mechanism (not shown) coupled to the plugging device via the cylinder 324 causes the balloon 332 to expand outwardly towards the endosteum 302, thereby deflecting the endosteum 302. As with the plugging devices shown in FIGS. 3B-C, the deflected endosteum 302 presses against the semicircular canal 306 and pins it against the opposite wall of the endosteum 302, thereby altering the canal's dimensions and constraining the flow of endolymph fluid 308 in the semicircular canal 306. As shown in FIG. 3D, the balloon 332 is actuated into a position whereby the semicircular canal is only partially pinched, and thus the motion of the endolymph fluid in the semicircular canal 306 is only partially constrained. However, the balloon 332 can be actuated to a position whereby the semicircular canal is substantially fully pinched, thus substantially precluding movement of the endolymph fluid in the semicircular canal 306.

The plugging device 330 includes a control mechanism (not shown) adapted to receive control signals from the control module 220 to cause the plugging device's pump to pump fluid to the extent required to inflate the balloon 332 to a set volume sufficient to pinch the canal. Thereafter, the volume of the balloon 332 is not altered except to adjust for minor changes to the volume of the balloon 332, or to adjust the volume of the balloon 332 in accordance with medical necessities.

The plugging devices shown in FIGS. 3B-3D are placed on the exterior of the endosteum. As a result, the endosteum 302 is not breached. This reduces the risk of damage that can otherwise be caused by the presence of a plugging device in the perilymph space.

Figure 3E:
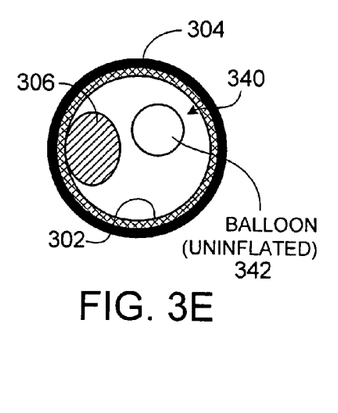
FIG. 3E is a schematic diagram in cross-section of an embodiment of a balloon plugging device implanted at the interior of the bony labyrinth.
Figure 3F:
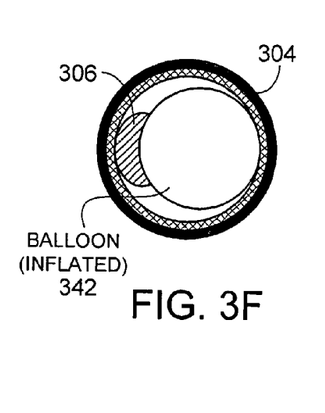
FIG. 3F is a schematic diagram in cross-section of the inflated balloon plugging device of FIG. 3E.

FIGS. 3E-F show, in cross-section, a fourth embodiment of a plugging device placed inside the perilymph space, thereby enabling the plugging device to directly exert pressure on the semicircular canal 306. As shown in FIG. 3E, a plugging device 340 includes a balloon 342 coupled to a balloon catheter (not shown). The balloon 342 is constructed of a durable, non-porous material having good elongation properties (e.g., greater than 250% of the original size of the balloon), and proper tensile strength. Example of such materials include latex, polyurethane, and silicone elastomers. It should be noted that if latex is selected, then medical grade latex, in which proteins causing allergic reaction have been removed, should preferably be used. A typical balloon 342 has a length of about 1 mm, an inflated circular cross-section diameter of 0.7-1 mm, and a deflated circular cross-section diameter of approximately 0.2-0.3 mm.

The balloon catheter is inserted into the perilymph space by cutting a small opening through the bony labyrinth 304 and the endosteum 302 and passing the balloon catheter into the perilymph space using a micromanipulator. After insertion of the balloon catheter, the openings in the bony labyrinth and endosteum are sealed and allowed to heal.

The plugging device 340 also includes a larger diameter catheter (not shown) located outside the bony labyrinth that is coupled to the smaller catheter that was inserted into the perilymph space. The larger catheter runs subcutaneously to a closed container in which a pump mechanism, a fluid reservoir for inflating the balloon, and a control mechanism to control the volume of the balloon 342 are all located. The pump mechanism, fluid reservoir, and the control mechanism are of conventional design and are therefore omitted from FIGS. 3E-F for the sake of clarity.

The control mechanism for the balloon plugging device shown in FIGS. 3E-F is adapted to receive control signals from the control module 220 and to cause the pump to pump fluid into the balloon 342 to inflate it.

As shown in FIG. 3F, the pump mechanism directs pressurized gas or liquid from the fluid reservoir through the interconnected catheters. This fluid inflates the balloon 342 inside the perilymph space. The balloon 342 then begins pressing against the semicircular canal 306, pushing it against the wall of the endosteum 302, thereby constraining the flow of the endolymph fluid through the semicircular canal 306. In FIG. 3F the balloon is shown as having been inflated to a volume that partially pinches the semicircular canal 306, and thus partially constrains movement of the endolymph fluid in the semicircular canal 306. To completely block the flow of the endolymph fluid in the semicircular canal 306, the balloon 342 is inflated further until it completely pinches the semicircular canal 306 and thus substantially blocks the flow of the endolymph fluid in the canal.

Once the balloon 342 has been inflated to its set volume inside the perilymph space, no additional fluid is pumped or withdrawn except to compensate for uncontrolled changes to the balloon's volume due, for example, to fluid leakage or to environmental changes (e.g., temperature and/or pressure changes), or to adjust the volume of the balloon in accordance with medical necessities. To deflate the balloon 342 so as to enable adjustments, or to remove the balloon 342 from the perilymph space, the pump mechanism withdraws the fluid inside the balloon 342.

The fluid reservoir used to inflate the balloon should have enough fluid to ensure that the balloon-based plugging device 340 will continue operating notwithstanding any fluid leakage. The fluid reservoir is preferably equipped with a recharging mechanism so that when the fluid level in the reservoir dips below a certain threshold level, the reservoir can be recharged to ensure continued operation of the plugging device 340.

It will be clear that the use of the pump mechanism together with the fluid reservoir described in relation to the plugging device 340 can also be used to control the operation of the plugging devices shown in FIGS. 3C and 3D.

Yet another embodiment of the plugging device 210 shown in FIG. 2, a piezoelectric device receives voltage control signals that cause it to be displaced so as to inwardly deflect the endosteum 302. The inward deflection of the endosteum consequently pinches the semicircular canal 306, and thus constrains the flow of endolymph fluid within it. Alternatively, the piezoelectric device could be used to push fluid to activate any of the plugging devices 322 332, 342 discussed previously. Alternatively, a piston could be forced against the endosteum 302 by the piezoelectric device.

Yet another embodiment uses a magnetic field created by a coil of wire to move a piston electromagnetically, which, in turn, pushes fluid to activate any of the plugging devices 322 332, 342 discussed previously. Alternatively, a piston moved by the magnetic coil could push directly on the endosteum 302.

As noted above, and as can be seen from FIGS. 3B-3F, the plugging device is adjacent to the endosteum 302. Placement of the plugging device either outside or inside the endosteum 302 generally includes a surgical procedure to, among other things, remove part of the bony labyrinth shielding the endosteum. Thus, performance of such a surgical procedure would generally require that at least local anesthesia be used.

Turning back to FIG. 2, although only a single plugging device 210 is shown, the vestibular canal plug apparatus may include additional plugging devices. For example, a companion plugging device (not shown in the figure) may be placed in the person's other ear. Or, more than one plugging device may be placed in each of a person's ears. For example, plugging devices may be placed in each of the three orthogonal semicircular canals forming a person's peripheral vestibular system.

As further shown in FIG. 2, coupled to the plugging device 210 is the control module 220. The control module 220 controls the actuated position of the plugging device. In particular, the control module sends control signals to the plugging device 210 that cause the plugging device 210 to move to a set actuated position. For a balloon-based plugging device, for example, the control signals cause the plugging device control mechanism to inflate the balloon to a set volume. As discussed above, the pre-determined set position or volume of the plugging device 210 pinches the semicircular canal 306 and thus reduces the volume in which the endolymph fluid can flow, thereby partially or completely constraining the movement of the endolymph fluid. This, in turn, reduces the sensitivity of the vestibular system to stimulation. Once the plugging device has been set to its actuated position, the control module 220 maintains the plugging device's actuation mechanism in its set position (or volume) and makes any necessary adjustments required by small deviations of the plugging device from its set actuated position.

Deviations from the plugging device's set actuated state generally occur because of fluctuations in external environmental factors or because of faults and imperfections of the plugging device. For example, where the plugging device 210 is a balloon-type plugging device (like the plugging device 330 shown in FIG. 3D), an ambient temperature variation of 5° C. can cause a 1% change in the ambient barometric pressure. Such a change in pressure can lead to unexpected and undesirable changes in the canal plug set point. In another example, the fluid in a balloon can leak, thereby decreasing the volume of a balloon-based plugging device.

To monitor changes to environmental conditions, the control module 220 includes a sensing system 222 that monitors exogenous conditions such as temperature, barometric pressure, etc. Additionally, the sensing system 222 also monitors the performance of the plugging device 210. For example, the sensing system can monitor and record the internal pressure of a balloon type plugging device, the position of a piston in the cylinder for a piston-based plugging device, etc. Other types of sensors may also be used.

As can further be seen in FIG. 2, the sensing system 222 is secured to the person's head. The relatively small size of the sensing system 222 enables placement of the sensing system 222 on the external surface of the head, preferably at an inconspicuous and unobtrusive location. Alternatively, the sensing system 222 may be placed underneath the surface of the head, or at other locations on the person's body.

The control module 220 also includes a computing device 224 that can perform computations using digital and/or analog techniques. The computing device 224 is configured to receive data from the various sensing devices of the sensing system 222, to process the data, and to generate output control information to be sent to the plugging device 210. Some operations that the computing device 224 is configured to perform include filtering and scaling of the input data. The computing device 224 processes the received data from the sensing devices and produces an output control feedback signal to maintain the plugging device in its actuated position.

The control device 220 also includes a user interface (not shown) to enable direct control by a user, such as the person wearing the plugging device, a physician, or a technician, to set the initial position/volume of the plugging device, or to change that set position at some later point should the person's medical condition require any such changes. Input entered through the user interface is processed by the computing device 224 to generate corresponding control signals for the plugging device 210. Typical user interfaces include a small key pad to enable the user to enter data. Such a key pad could be attached to a housing in which the computing device 224 is held. However, the user interface need not be located proximate to the computing device 224. For example, a computer console can be remotely linked to the computing device 224, either using wireless transmission, or by direct physical coupling. Executing on such a computer console would be, for example, a graphical user interface to enable the user to enter the data for controlling the actuated position of the plugging device 210.

The computing device 224 thus sends initial control signals to the plugging device 210 to cause the plugging device to move to its initial set actuated position. Subsequently, the computing device 224 generates control signals to maintain the plugging device 210 in its set actuated position, and/or to change the set actuated position as may be decided by a user from time to time.

The computing device 224 may include a computer and/or other types of processor-based devices suitable for multiple applications. Such devices can include volatile and non-volatile memory elements, and peripheral devices to enable input/output functionality. Such peripheral devices include, for example, a CD-ROM drive and/or floppy drive, or a network connection, for downloading software containing computer instructions to enable general operation of the processor-based device, and for downloading software implementation programs to receive and process sensor data and user data, and generate corresponding control information to control the plugging device. Additionally or alternatively, the computing device 224 may include a digital signal processor (DSP) to perform the various processing functions described above. A suitable DSP is the Analog Devices ADSP 2183 processor.

The computing device 224 is placed proximate to the sensing system 222, thereby minimizing the distance that signals from the sensing devices travel to reach the computing device 224. Thus, in FIG. 2 the computing device 224 is shown located on the wearer's head. However, the location of the computing device 224 is not critical. The device 224 can thus be placed anywhere on the person's body, or even at a location not on the person's body.

FIG. 2 further shows that the vestibular canal plug apparatus also includes a power source 230 to power both the sensing system 220 and/or the plugging device 210. The power source 230 may be a battery carried or attached to the person. The power source 230 is electrically coupled to the sensing system 220 and/or the plugging device 210 using electrical conducting wires. Since the plugging device 210 is generally implanted internally near the person's vestibular system, the electrical power wires pass subcutaneously en route to the plugging device 210. Alternatively, powering of the control module 220 and the plugging device 210 may be implemented through power telemetry, in which power is delivered to the plugging device 210 and/or the sensing system 220 via wireless power transmission. In some embodiments the power source 230 may include several independent power units. For example, a battery for delivering sufficient power to the control module 220 could be connected directly to the control module 220 via electrical wires. A separate power unit, situated at a different location, could be used, for example, to deliver power to the plugging device 210 using power telemetry.

Some embodiments may not require a power source. For example, passive pressure regulation can be provided via a pressure regulator.

Typically, the apparatus 200 has to be calibrated. Calibration of the apparatus 200 can include calibrating the sensing system 222 to ensure the accuracy of the sensing devices' measurements. Additionally, calibration of the apparatus 200 includes determining how fluctuating external environmental conditions affect the performance of the plugging device 224 (e.g., how a change of the outside temperature would affect fluid pressure inside a balloon). Determining those relationships enables the computing device 224 to compute the extent of adjustment required to restore the plugging device to its actuated set position.

In operation, a plugging device 210 is implanted proximate to a semicircular canal in the person's vestibular system. At some later point, after the person has sufficiently recovered from the surgical procedure for implanting the plugging device, the actuated position of the plugging device 210 is determined. This is typically done by experimentally adjusting the actuated position of the plugging device (e.g., varying the volume of a balloon-based plugging device) while measuring responses like perception of motion, eye responses, or changes in actuator pressure for different amounts of actuation. Experimental adjustment of the actuated position of the plugging device 210 can also be done in accordance with observed improvements of the vertiginous symptoms experienced by the patient. The determination of the set position of the plugging device 210 is generally performed by entering data through a user interface linked to the control module 220 to generate control signals that move the plugging device to a particular position. Feedback from the sensors or from the patient regarding the comfort level and effectiveness of the plugging device at that actuated position is used to iteratively adjust the position of the plugging device until the optimal actuated position of the plugging device 210 is determined. In its optimal actuated position, the plugging device 210 constrains, either partially or fully, the movement of the endolymph fluid in a semicircular canal upon which it acts.

Once the plugging device 210 has been actuated to its optimal set position, the control module receives sensory data from the various sensing devices of the sensing system 222. The computing device 224 uses that data to determine if the plugging device has deviated from its actuated position. The computing device 224 then determines any minute adjustments that may be needed to restore the plugging device 210 to its set actuated position, and generates corresponding control signals that are sent to the plugging device. The control signals cause the plugging device 210 to make the necessary adjustments to its position.

To change the set actuated position of the plugging device 210, or to disable it (i.e., retract the plugging device to a non-actuating position in which no pressure is exerted on the semicircular canal), a user can manually make that change. The user's input is entered through a user interface connected to the control module 220, and the computing device 224 uses the input to generate a corresponding control signal. The control signal is sent to the plugging device 210 and causes the plugging device 210 to move to a different set position, or to withdraw the plugging device 210 to a non-actuating position. For example, in a balloon-based plugging device, such as the plugging device 340 in FIG. 3E, a control signal to disable the device causes the plugging device to withdraw fluid from the balloon 342 to deflate it, and thus retract it to a non-actuating position.

To completely remove the plugging device 210, the plugging device 210 is first disabled and subsequently surgically removed, enabling the patient to regain his regular vestibular functions.

Although FIG. 2 shows the apparatus 200 being used with a human being, the apparatus 200 can also be used with animals. The apparatus 200 need not be used to only alleviate medical conditions related to a person's vestibular system, but can be used to remedy other medical conditions in which reduction of the sensitivity of the vestibular system to stimulation is desirable. Further, the apparatus 200 may be used for non-therapeutic or even non-medical purposes. For example, the apparatus 200 can be used in the course of medical research to investigate the functioning of the brain.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:
1. A method for reducing sensitivity of a vestibular system in a patient to stimulation, the method comprising:
  inserting a plugging device in direct contact with an endosteum membrane of a semicircular canal of a patient;
  actuating the plugging device to a selected one of multiple possible actuated positions that cause a hollow space within the semicircular canal to be reversibly deformed by a variable extent by pressing directly on the endosteum membrane, the selected one of multiple possible positions causing the hollow space within the semicircular canal to be deformed to an extent in which movement of endolymph fluid in the semicircular canal is completely blocked;
  determining, by a computing device, a deviation of the plugging device from the selected actuated position; and
  providing a control signal in response to the determined deviation to maintain the plugging device at the selected actuated position to completely constrain the movement of the endolymph fluid in the semicircular canal.

2. The method of claim 1, further comprising:
receiving data indicative of at least one of: environmental conditions, and performance of the plugging device; and
generating the control signal on the basis of determining the deviation computed from the received data, wherein the control signal causes the plugging device to maintain the selected actuated position.

3. The method of claim 1, further comprising causing the plugging device to move to the selected actuated position.

4. The method of claim 3, wherein causing the plugging device to move to the selected actuated position comprises causing a balloon to change its volume.

5. The method of claim 3, wherein causing the plugging device to move to the selected actuated position comprises causing an elastic membrane to expand.

6. The method of claim 4, wherein maintaining the balloon at the selected actuated position comprises changing the volume of the balloon in response to at least one of: fluid leakage from the balloon, and air pressure changes.

* * * * *

UNITED STATES PATENT AND TRADEMARK OFFICE
CERTIFICATE OF CORRECTION

PATENT NO. : 8,430,823 B2  
APPLICATION NO. : 13/233111  
DATED : April 30, 2013  
INVENTOR(S) : Daniel Michael Merfeld et al.

Page 1 of 1

It is certified that error appears in the above-identified patent and that said Letters Patent is hereby corrected as shown below:

In the Specification

Column 1, Line 10, please insert the following paragraph:
--GOVERNMENT RIGHTS
This invention was made with government support under Grant Number DC003066 awarded by the National Institutes of Health. The government has certain rights in the invention.--

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*